United States Patent [19]

Angus et al.

[11] Patent Number: 4,828,494

[45] Date of Patent: May 9, 1989

[54] TOOTH FRACTURE FINDER

[75] Inventors: William H. Angus; Everett C. Grollimund, both of Midlothian, Va.

[73] Assignee: Dental Design Systems, Inc., Midlothian, Va.

[21] Appl. No.: 921,249

[22] Filed: Oct. 21, 1986

[51] Int. Cl.⁴ ............................................. A61C 5/00
[52] U.S. Cl. ................................... 433/215; 433/141
[58] Field of Search ................... 433/215, 72, 75, 229, 433/141; 128/25 R, 62 A, 777; 272/95

[56] References Cited

U.S. PATENT DOCUMENTS

| | | | |
|---|---|---|---|
| 1,749,632 | 3/1930 | Ferris | 128/62 A |
| 1,869,391 | 8/1932 | Quintina | 272/95 |
| 2,937,446 | 5/1960 | Weisenfeld | 433/141 |
| 3,293,748 | 12/1966 | Skinner | 128/62 A |
| 3,734,081 | 5/1973 | Schaack | 433/215 |
| 3,903,606 | 9/1975 | Oliver | 433/141 |
| 4,500,294 | 2/1985 | Lewis | 433/215 |
| 4,541,803 | 9/1985 | Adler | 433/141 |

*Primary Examiner*—John J. Wilson
*Attorney, Agent, or Firm*—John F. C. Glenn

[57] ABSTRACT

A ball at one end of a handle has opposite indentations to receive the ends of cusps of opposed teeth of a patient. The other end of the handle is flattened to help position the ball. When the patient bites against the ball, a crack in a tooth near a cusp against the ball will cause pain and thereby indicate the location of a crack.

6 Claims, 1 Drawing Sheet

TOOTH FRACTURE FINDER

BACKGROUND OF THE INVENTION

When a dentist suspects that a patient is suffering from a fractured bicuspid or molar posterior tooth, the problem is to identify which tooth is fractured and where the fracture is within the tooth. X-rays are generally used as part of the diagnostic procedures, but generally the dentist will not be able to see the fracture on X-rays because the fracture is too fine to be seen on radiographs. Therefore, a diagnostic tool is needed for specifically locating a fracture in posterior teeth which is not obvious on the basis of clinical examination.

SUMMARY OF THE INVENTION

The present invention provides a tool for finding a fracture in posterior teeth quickly and inexpensively. The tool comprises a bit-resistant ball small enough to fit between two opposed posterior teeth and having indented ends where each indentation can capture the projecting end of a cusp of a tooth. One cusp of each of a pair of opposed posterior teeth engage the ball and center it between the two opposed teeth. A handle extends from the ball, long enough to be grasped by a pair of opposed fingers of the dentist or the patient himself searching for a fracture in a tooth. The finger-held end of the handle is flattened and preferably ribbed to facilitate holding it while the ball at the other end of the handle is moved into position between successive pairs of teeth. When the patient bites down on the ball the resultant pressure produces pain or discomfort where the cusp closest to the fracture is against the ball. Thus, each of the two cusps of each bicuspid and each of the several cusps of each molar can be tested for an adjacent facture by biting down on the ball each time it is placed between successive pairs of different opposed cusps. This will produce the desired preliminary identification, subject to subsequent conventional procedures to confirm the finding.

BRIEF DESCRIPTION OF THE DRAWING

Referring now to the accompanying drawing, in which there is shown, for purposes of illustration only, the present preferred embodiment of the invention.

DETAILED DESCRIPTION OF THE PRESENT PREFERRED EMBODIMENT

Figure 3:
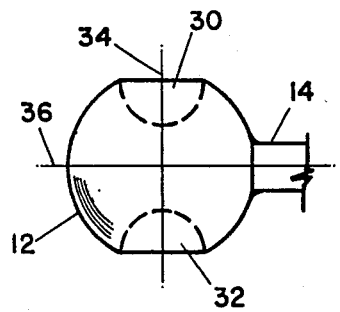
FIG. 3 shows a view corresponding to FIG. 1, but enlarged and broken away showing the back of the left end of FIG. 1.
Figure 1:
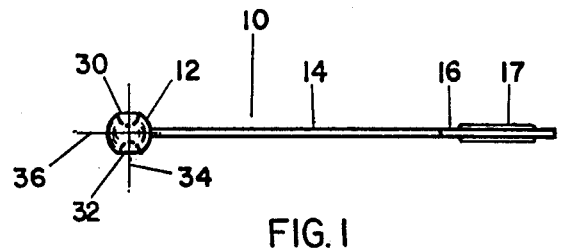
FIG. 1 shows a side plan view of a tool embodying the invention.
Figure 4:
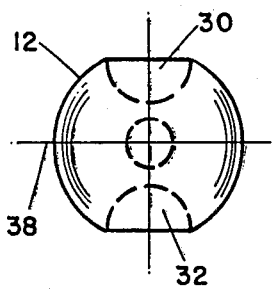
FIG. 4 shows an end view of what is shown in FIG. 3, as seen from the left of FIG. 3.
Figure 2:
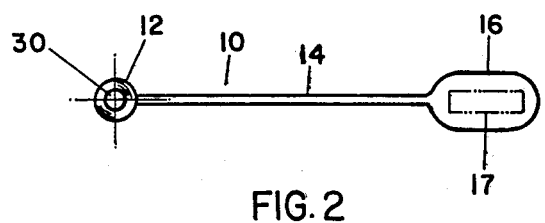
FIG. 2 shows a top plan view of the tool shown in FIG. 1.
Figure 5:
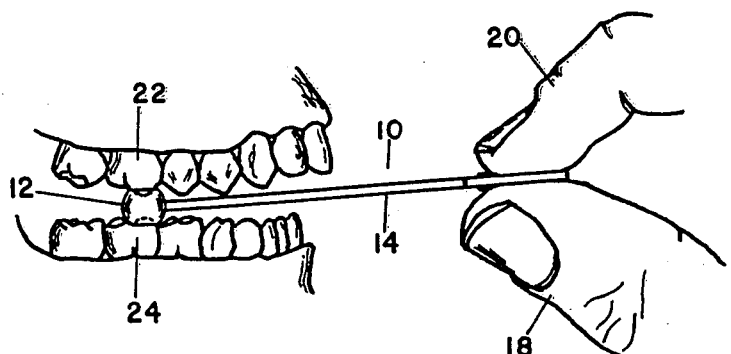
FIG. 5 shows a semi-diagramatic and partially broken away view of the tool in use between a pair of teeth of a patient while the handle is held by the fingers of a patient or dentist.

Referring now more particularly to the drawings, the illustrated tool 10 has a bite-resistant ball 12 secured to one end of a handle 14. The other end of the handle terminates in a flattened portion 16 adapted to be held between a thumb 18 and forefinger 20 of a dentist or patient while the ball 12 is maneuvered into postion between a pair of opposed teeth 22 and 24 of a patient, where the projecting end of one cusp of the upper tooth 22 extends into the upper indentation 30 of the ball, and the projecting end of one cusp of the lower tooth 24 extends into the lower indentation 32 of the ball. The patient is then asked to bite down on the ball. If either of the teeth has a fracture adjacent to the cusp of that tooth in one of the indentations 30 or 32, biting down on the ball will produce a pain or discomfort which will identify the cusp adjacent to a fracture. All of the opposed pairs of teeth can be successively tested with little trouble in a short time. Once the troublesome tooth or teeth have been located, conventional procedures can be used for confirmation and more detailed diagnosis preliminary to remedial treatment of the tooth or teeth identified as troublesome by the bite test.

The flattened handle portion 16 is preferably provided with ribs 17 to minimize slippage of the flattened portion 16 between fingers grasping it. The ribs can take the form of raised print showing a supplier's name or trade mark.

The whole tool 10 is preferably cast as a unit from a polymeric material capable of forming a ball hard enough to survive multiple bites between human teeth, and to provide sufficient bite resistance to cause a fractured tooth to give a distinctively strong reaction. A shore hardness of about 72 is preferred, although a wider range, such as 69 to 75 shore hardness, may be used. Nylon is a typical polymer suitable for the purpose. Other material can also be used, such as alloys of gold or silver which are hard enough for the purpose, but not so hard as to unduly risk injury to the surface of teeth being tested.

The test ball is preferably of solid spheroidal form of about 0.3 inch diameter and having a pair of oppositely opening indentations 30 and 32 of hemispherical shape and positioned at opposite ends of an axis 34 extending through the center of the ball. In the present preferred practice the said hemispheric indentations have a radius of about 5/64 inch, so that this diameter at the outer surface of the ball is about 5/32 inch and their depth is about 5/64 inch. The handle 14 extends along a straight line 36 which when extended intersects said common axis at right angles thereto, and the flattened handle portion 16 lies in a plane 38 which is also normal to said common axis.

The whole tool 10 is preferably about 2½ inches long. Flattening the finger-held end of the handle, while not essential, is useful to facilitate maneuvering the tool without dropping it, and to aid in orienting the ball for proper positioning of its indentations between the teeth. For this purpose the flattened end should extend normal to the said axis 34 through the indentation 30 and 32.

While a present preferred embodiment of the invention has been illustrated and described, it will be understood that the invention may be otherwise variously embodied and practiced within the scope of the following claims.

We claim:

1. A tool for testing human posterior teeth for fractures, comprising a bite-resistant ball adapted to be pressed between a pair of opposed human posterior teeth in a mouth, and a handle secured to and extending from the ball far enough to be grasped at the far end by fingers outside of the mouth, said ball having a pair of indentations on opposite sides of the ball and aligned with opposite sides of an axis through the center of the ball, each indentation providing means for receiving the projecting end of only a single tooth cusp at a time; and said ball being hard enough to cause pain in a tooth having a crack adjacent to a cusp biting against the ball while in one of said indentations.

2. A tool according to claim 1 in which the far end of the handle is flattened and ribbed to facilitate grasping it, and in which said tool is a single solid unit of cast polymeric material.

3. A tool according to claim 2, in which said handle is flat in a plane substantially normal to said axis of the opposite indentations in the ball.

4. A tool for testing human posterior teeth for fractures, comprising a bite-resistant ball adapted to be pressed between a pair of opposed human posterior teeth in a mouth, and a handle secured to and extending from the ball far enough to be grasped at the far end by fingers outside of the mouth, said ball having a pair of indentations on opposite sides of an axis through the center of the ball, each indentation providing means for receiving the projecting end of only a single tooth cusp at a time; said tool being a single solid unit of cast polymeric material; and said ball being hard enough to cause pain in a tooth having a crack adjacent to a cusp biting against the wall while in one of said indentations.

5. A tool according to claim 4, said unit of cast polymeric material having a Shore hardness of about 69 to 75.

6. A tool according to claim 5, in which the cast polymeric material is nylon.

* * * * *